s)undecane) J. Chem. Soc., Perkin Trans. I, pp. 789-792 (1975).

Koch, Herbert et al., "Carbonsauresynthese in der Bicycloheptane und Tricyclodecan Reihe." Liebigs Annalen, vol. 638 (1960), pp. 111-121.

Kirk-Othmer, "Encyclopedia of Chemical Technology," 2nd Ed. Supp. vol., pp. 5-13 (1972), Interscience Publ.

*Primary Examiner*—James O. Thomas, Jr.
*Assistant Examiner*—L. Hendriksen
*Attorney, Agent, or Firm*—Oblon, Fisher, Spivak, McClelland & Maier

[57] ABSTRACT

Tricyclo[4.3.1.1$^{2,5}$]undecane-1-carboxylic acid and acid halides and esters thereof having the formula (I),

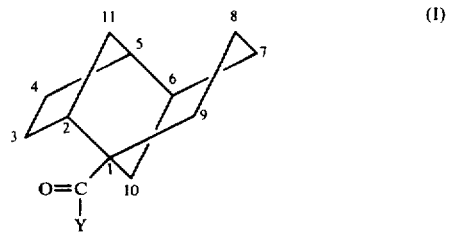

wherein Y represents a hydroxy group, a chlorine or bromine atom, or an alkoxy group of the formula RO— wherein R is a straight-chain, branched-chain or cyclic alkyl group having 1 to 12 carbon atoms, include compounds which exhibit superior antiviral action.

2 Claims, No Drawings

United States Patent [19]

Aigami et al.

[11] 4,169,953
[45] Oct. 2, 1979

[54] TRICYCLO[4.3.1.1$^{2,5}$]UNDECANE-1-CARBOXYLIC ACID AND DERIVATIVES THEREOF AND A PROCESS FOR PRODUCING THE SAME

[75] Inventors: Koji Aigami; Yoshiaki Inamoto; Motoyoshi Ohsugi; Yoshiaki Fujikura, all of Wakayama; Naotake Takaishi, Sakura, all of Japan

[73] Assignee: Kao Soap Co., Ltd., Tokyo, Japan

[21] Appl. No.: 917,253

[22] Filed: Jun. 20, 1978

[30] Foreign Application Priority Data

Jun. 21, 1977 [JP] Japan ............................ 52/72768
Jun. 21, 1977 [JP] Japan ............................ 52/72769
Jul. 4, 1977 [JP] Japan ............................ 52/79749

[51] Int. Cl.$^2$ .................... C07C 69/74; A61K 31/215
[52] U.S. Cl. .................................. 560/117; 562/499; 260/544 L; 424/305
[58] Field of Search ................ 562/499; 560/117; 260/544 L

[56] References Cited

U.S. PATENT DOCUMENTS

4,002,674   1/1977   Inamoto et al. .................. 560/117
4,070,540   1/1978   Inamoto et al. .................. 560/117

FOREIGN PATENT DOCUMENTS

51-13760   2/1976   Japan .

OTHER PUBLICATIONS

Takaishi, Naotake et al., "Synthesis and Acid-catalyzed Rearrangement of (1R,2R,5S,6S)-Tricyclo(4.3.1.1$^{2,}$-

TRICYCLO[4.3.1.1$^{2,5}$]UNDECANE-1-CARBOXYLIC ACID AND DERIVATIVES THEREOF AND A PROCESS FOR PRODUCING THE SAME

BACKGROUND OF THE INVENTION

1. Field of the Invention

This invention relates to the novel tricyclo[4.3.1.1$^{2,5}$]-undecane-1-carboxylic acid and acid halides and esters thereof represented by the formula (I),

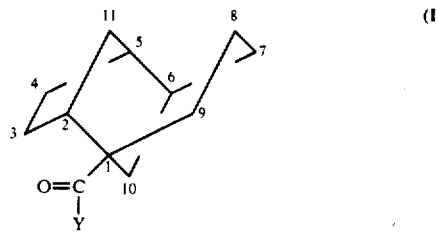

wherein Y represents a hydroxy group, a chlorine or bromine atom, or an alkoxy group of the formula RO- wherein R is a straight-chain, branched-chain or cyclic alkyl group having 1 to 12 carbon atoms.

2. Description of the Prior Art

The carbon framework of compounds represented by the formula (I), tricyclo[4.3.1.1$^{2,5}$]undecane, was first found as an isomerized intermediate by Takaishi et al [N. Takaishi, et al., J. Chem. Soc., Perkin Trans. I, 789 (1975)]. However, no attempt has been made to study derivatives of tricyclo[4.3.1.1$^{2,5}$]undecane.

The present inventors have made a wide variety of studies on such derivatives and, as a result, have succeeded in synthesizing the novel compound of the formula (I), and testing their pharmacological activities.

SUMMARY OF THE INVENTION

One object of this invention is to provide tricyclo-[4.3.1.1$^{2,5}$]undecane-1-carboxylic acid and and halides thereof which are useful as starting materials for the manufacture of medicinal compounds.

Another object of this invention is to provide tricyclo-[4.3.1.1$^{2,5}$]undecane-1-carboxylic acid alkyl esters possessing excellent antiviral action.

A further object of this invention is to provide a novel process for producing the above tricyclo[4.3.1.1$^{2,5}$]undecane-1-carboxylic acid, acid halides thereof and alkyl esters thereof.

DETAILED DESCRIPTION OF THE PREFERRED EMBODIMENTS

The compound of the formula (I) wherein Y is a hydroxy group, tricyclo[4.3.1.1$^{2,5}$]undecane-1-carboxylic acid of the formula (Ia),

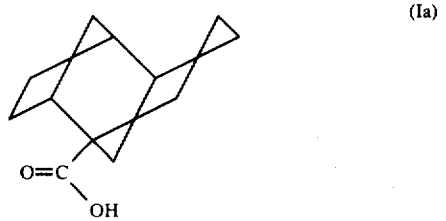

can be used as a starting material for the manufacture of 1-aminomethyltricyclo[4.3.1.1$^{2,5}$]undecane or an acid addition salt thereof which is useful as an antiviral agent, as disclosed in Applicants' copending application Ser. No. 920,967. 1-Aminomethyltricyclo[4.3.1.1$^{2,5}$]undecane can be produced, for instance, by producing tricyclo[4.3.1.1$^{2,5}$]undecane-1-carboxylic acid amide or 1-cyanotricyclo[4.3.1.1$^{2,5}$]undecane from the compound of the formula (Ia) by conventional methods, and reducing the resulting compound.

The compound of the formula (I) wherein Y is a chlorine or bromine atom, 1-chloro- or 1-bromo-carbonyltricyclo[4.3.1.1$^{2,5}$]-undecane of the formula (Ib),

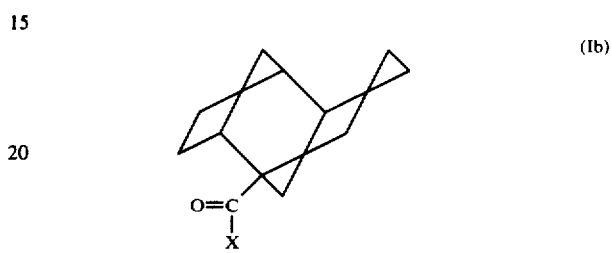

wherein X represents a chlorine or bromine atom, is useful as an intermediate for the production of medicines. 1-Aminomethyltricyclo[4.3.1.1$^{2,5}$]undecane which is useful as an antiviral agent can be easily produced as for example by reacting the compound of the formula (Ib) with ammonia to form the aforementioned tricyclo[4.3.1.1$^{2,5}$]undecane carboxylic acid amide, and reducing the amide.

The compound of the formula (I) wherein Y represents an alkoxyl group of the formula of RO- wherein R is a straight-chain, branched-chain or cyclic alkyl group having 1 to 12 carbon atoms, 1-alkoxycarbonyltricyclo[4.3.1.1$^{2,5}$]undecane of the formula (Ic),

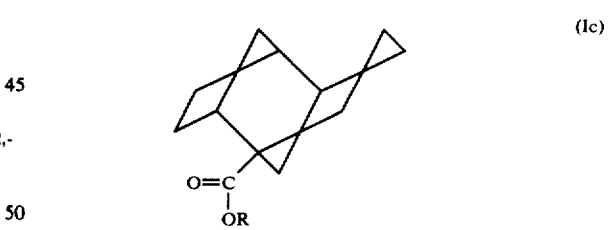

exerts an excellent inhibitory effect on the progression of Newcastle disease caused by Paramyxo virus, belonging to the class of RNA viruses, in the embryonal cells of chickens, and presents less cytotoxicity at an effective concentration; that is, the compound of the formula (Ic) can inhibit the growth of viruses in a concentration ranging from 1/6 to ⅔ in terms of its ratio to adamantylamine hydrochloride which is known to be an anti-influenza viral agent. Thus, the compound of the formula (Ic) is very useful as a medicine or drug for animals.

The carboxylic acid and a derivative thereof of the formula (I) can be, for instance, produced according to the following scheme:

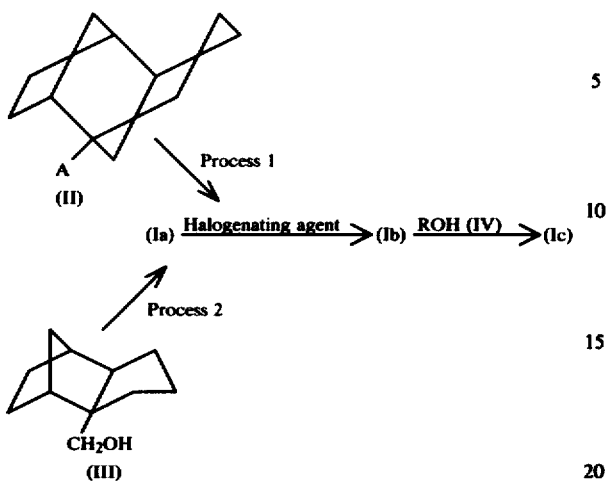

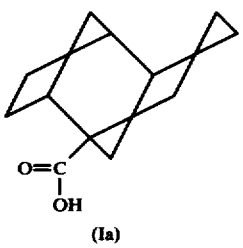

wherein A represents a bromine or chlorine atom, or hydroxyl group. The present compound of the formula (Ia) can be produced by Process 1 or Process 2.

Process 1

According to the following reaction scheme, tricyclo[4.3.1.1$^{2,5}$]undecane-1-carboxylic acid of the formula (I) is produced by reacting 1-halogeno (or hydroxy) tricyclo-[4.3.1.1$^{2,5}$]undecane of the formula (II) with sulfuric acid and formic acid.

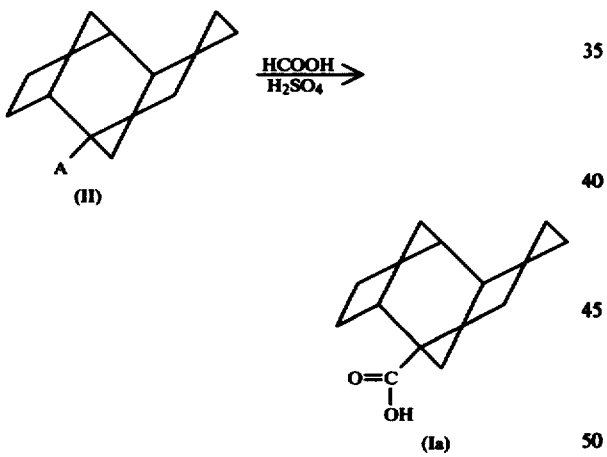

wherein A represents a bromine or chlorine atom, or a hydroxyl group.

Process 2

According to the following reaction scheme, tricyclo[4.3.1.1$^{2,5}$]undecane-1-carboxylic acid of the formula (Ia) is produced by reacting endo-2-hydroxymethyl-tricyclo[5.2.1.0$^{2,6}$]-decane of the formula (III) with sulfuric acid and formic acid.

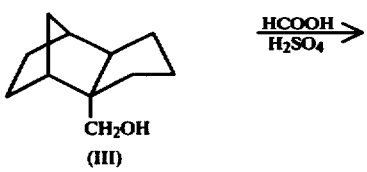

The compound of the formula (III), the starting material in Process 2, can be easily produced, according to the following reaction scheme, by subjecting exo-2-hydroxy-exo-5,6-trimethylenenorbornane of the formula (V) to Koch's carboxylation reaction to form endo-2-carboxy-exo-2,3-trimethylenenorbornane of the formula (VI) [Koch et al., Liebigs Annalen, 638, 111 (1960)], and reducing the resulting compound with lithium aluminum hydride or the like.

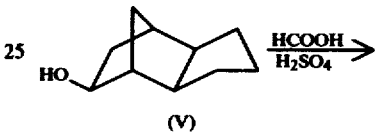

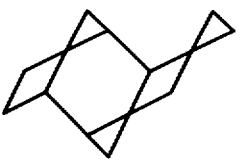

The compound of the formula (II), the starting material in Process 1, can be for instance easily produced by treating endo-2-hydroxymethyltricyclo[5.2.1.0$^{2,6}$]decane of the formula (III) with a hydride donor and an acid catalyst to produce tricyclo[4.3.1.1$^{2,5}$]undecane of the formula (VII) (Japanese Patent Application No. 51-13760), reacting the resulting compound with bromine in the presence of sulfuric acid to produce 1-bromotricyclo[4.3.1.1$^{2,5}$]undecane (II, A=Br), hydrolyzing the resulting compound to produce 1-hydroxytricyclo-[4.3.1.1$^{2,5}$]undecane (II, A=OH), and reacting the resulting compound with a chlorinating agent such as thionyl chloride to produce 1-chlorotricyclo[4.3.1.1$^{2,5}$]undecane (II, A=Cl).

As described above, Koch's reaction is applied to both cases of Process 1 and Process 2 which are carried out by reacting the starting materials of the formulae (II) and (III) with sulfuric acid and formic acid. 3 to 50 moles of sulfuric acid and 1 to 30 moles of formic acid are preferably used per mole of the compounds of the formulae (II) and (III). It is preferable to conduct the present reaction at a temperature of −20° to +40° C., particularly −10° to +30° C. Suitable solvents for the reaction include n-hexane, n-pentane, n-heptane, cyclohexane and benzene which do not participate in the reaction.

The compound of the formula (Ib) is, for instance, produced by reacting 1-carboxytricyclo[4.3.1.1$^{2,5}$]undecane of the formula (Ia) with a halogenating agent.

Suitable halogenating agents include a phosphorus halogenide such as phosphorus trichloride, phosphorus tribromide, phosphorus pentachloride and phosphorus pentabromide; and a thionyl halide such as thionyl chloride and thionyl bromide. The reaction is carried out in an inert solvent under reflux conditions.

The thus obtained compound of the formula (Ib) was identified by first ascertaining the compound to be a corresponding acid halide by elemental analyses. The compound showed absorption peaks at 3010~3030 cm$^{-1}$ in its infrared absorption spectrum which were characteristic of the carbon framework of a compound of the formula (I). Further, there was absorption in the vicinity of 1800 cm$^{-1}$ due to the carbonyl group of the acid halide. The hydrolyzed product of the compound was confirmed to be identical with the starting material, 1-carboxytricyclo[4.3.1.1$^{2,5}$]undecane. The structure of the compound was determined by the above data.

1-Alkoxycarbonyltricyclo[4.3.1.1$^{2,5}$]undecane of the formula (Ic) is produced, according to the following scheme, by reacting tricyclo[4.3.1.1$^{2,5}$]undecane-1-carboxylic acid halide of the formula (Ib) with an alcohol of the formula (IV),

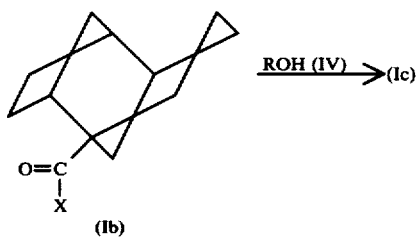

wherein X represents a bromine or chlorine atom, and R is the same as above.

Suitable alcohols of the formula (IV) include a primary alcohol having a straight-chain, branched-chain or cyclic alkyl group of 1 to 12 carbon atoms, such as methyl alcohol, ethyl alcohol, n-propyl alcohol, i-propyl alcohol, n-butyl alcohol, s-butyl alcohol, i-butyl alcohol, t-butyl alcohol, amyl alcohol, hexyl alcohol, octyl alcohol, decyl alcohol, lauryl alcohol, 2-ethylhexyl alcohol, cyclopentanol, cyclohexanol, norbornyl alcohol and 5,6-trimethylenenorbornan-2-ol.

In producing the desired compound of the formula (Ic) from the compound of the formula (Ib), the alcohol of the formula (IV) is used in an equivalent or excess amount, preferably from 1 to 100 moles per mole of the compound of the formula (Ib). The reaction is preferably conducted at a temperature from 0° to 100° C., particularly 20° to 50° C. In order to accelerate the reaction velocity, a basic catalyst such as pyridine or triethylamine is added, preferably from 1 to 20 moles per mole of the acid halide of the formula (Ib). When the alcohol of the formula (IV) possesses sufficient fluidity, there is no need to use a solvent. If necessary, a solvent which does not participate in the reaction, such as ether, chloroform, methylene chloride or benzene may be used.

The structure of the present compound of the formula (Ic) was determined as follows: the molecular formula was first determined by elemental analyses and mass spectra. Further, absorption peaks were observed at 1720 cm$^{-1}$ due to the ester group and at 3010~3030 cm$^{-1}$ characteristic of tricyclo-[4.3.1.1$^{2,5}$]undecane which is due to the C-H stretching vibration in the infrared spectrum.

The present compound of the formula (Ic) was examined for the pharmacological effects as shown below.

After a monolayer culture of chick embryo fibroblasts cells was cultivated in a test tube for 2 to 3 days, it was inoculated with a Newcastle disease virus solution having about 128 HAU (hemagglutination unit) and one of a series of serially diluted solutions of the test compounds, as disclosed in Applicants' copending application Ser. No. 920,967 and the virus multiplication was measured by a hemagglutination test. The results obtained are shown in Table 1.

Table 1

| Test Compounds | | MIC | MCC |
| R in the formula(I) | | (μg/ml) | (μg/ml) |
| --- | --- | --- | --- |
| Present Compounds | CH$_3$ | 200 | 200 |
| | n-C$_4$H$_9$ | 40 | 200 |
| | n-C$_8$H$_{17}$ | 200 | 1000 |
| | (cyclobutyl) | 40 | 200 |
| | (cyclohexyl, H) | 200 | 200 |
| | (bicyclic) | 200 | 1000 |
| Control | Adamantylamine hydrochloride (NH$_2$·HCl) | 250 | 250 |

The invention is illustrated below in further detail with reference to the Examples, but the invention is not limited to the Examples.

EXAMPLE 1

50 g of endo-2-hydroxymethyltricyclo[5.2.1.0$^{2,6}$]decane dissolved in 200 ml of formic acid was added dropwise with stirring to 400 ml of conc. sulfuric acid over a period of 2.5 hours while the temperature was kept at 0° to 10° C. The mixture was further stirred for 1 hour and allowed to stand. Separated solids were collected by filtration, washed with water and dried to afford 58.2 g (yield: 99.6%) of tricyclo-[4.3.1.1$^{2,5}$]undecane-1-carboxylic acid of the formula (Ia). Recrystallization from n-hexane yielded white crystals having a melting point of 158.5° to 159.5° C.

Elemental Analysis; as C$_{12}$H$_{18}$O$_2$: Calculated: C, 74.19; H, 9.34%: Found: C, 74.0; H, 9.24%:

IR (KBr); 3300~2700, 1685, 1460, 1405, 1290, 1270 cm$^{-1}$.

Mass Spectrum m/e (relative intensity); 194 (M+, 21), 149 (36), 127 (40), 126 (25), 123 (26), 107 (15), 95 (20).

13CNMR (CDCl3, δC); 18.2 (t), 26.2 (t), 26.7 (t+t), 28.1 (t), 30.9 (t), 32.4 (d), 40.3 (d), 42.9 (d), 44.9 (s), 185.6 (s).

EXAMPLE 2

5 g of 1-hydroxytricyclo[4.3.1.1$^{2,5}$]undecane dissolved in 20 ml of formic acid was added dropwise with stirring to 40 ml of conc. sulfuric acid over a period of 1.5 hours while the temperature was kept at 0° to 10° C. The mixture was further stirred for 1 hour and allowed to stand. Separated solids were collected by filtration and dried to afford 5.7 g (yield: 97.5%) of tricyclo[4.3.1.1$^{2,5}$]undecane-1-carboxylic acid of the formula (1a). The data on the melting point, elemental analysis, IR, MS and $^{13}$C NMR spectra were in complete agreement with that in Example 1.

EXAMPLE 3

6.9 g of 1-bromotricyclo[4.3.1.1$^{2,5}$]undecane dissolved in 20 ml of formic acid was added dropwise to 40 ml of conc. sulfuric acid under the same conditions as in Example 2, and the resulting mixture was treated in the same manner as in Example 2 to afford 5.5 g (yield: 94.0%) of the crystals of tricyclo[4.3.1.1$^{2,5}$]undecane-1-carboxylic acid of the formula (1a). The melting point, elemental analysis, IR, MS and $^{13}$C NMR spectra were in accord with those in Example 1.

EXAMPLE 4

68 ml of thionyl chloride was added dropwise to 46.0 g (0.24 mole) of 1-carboxytricyclo[4.3.1.1$^{2,5}$]undecane dissolved in 200 ml of benzene at room temperature. The resulting mixture was refluxed for 1.5 hours, and the excess thionyl chloride and benzene were distilled off under reduced pressure. The residue obtained was fractionally distilled under reduced pressure to afford 47.0 g (yield: 92%) of 1-chorocarbonyltricyclo[4.3.1.1$^{2,5}$]undecane having a boiling point of 101° c. (1 mmHg).

Elemental Analysis; as $C_{12}H_{17}OCl$: Calculated: C, 67.76; H, 8.06; Cl, 16.67%: Found: C, 16.61; H, 8.12; Cl, 16.82%.

IR (neat); 3030, 2930, 2875, 2790, 2750 (sh), 1480, 990, 940, 860, 840, 740 cm$^{-1}$.

EXAMPLE 5

3 g of thionyl bromide was added dropwise with stirring to 2.0 g (10.3 mmoles) of 1-carboxytricyclo[4.3.1.1$^{2,5}$]undecane dissolved in 20 ml of anhydrous benzene at room temperature. The mixture was heated under reflux for 1.5 hours. After cooling, the excess thionyl bromide and benzene were distilled off under reduced pressure. The residue obtained was distilled under reduced pressure to afford 2.0 g (yield: 75.5%) of 1-bromocarbonyltricyclo[4.3.1.1$^{2,5}$]undecane having a boiling point of 116° C. (1 mmHg).

Elemental Analysis; $C_{12}H_{17}OBr$: Calculated: C, 56.05; H, 6.66; Br, 31.07%: Found: C, 56.21; H, 6.52; Br, 31.57%.

IR (neat); 3010, 2900, 2830, 1795, 1680, 1460, 920, 820, 720 cm$^{-1}$.

EXAMPLE 6

1.0 mole of 1-chlorocarbonyltricyclo[4.3.1.1$^{2,5}$]undecane dissolved in 300 ml of anhydrous ether was added dropwise with stirring to a mixture of 1.1 moles of an alcohol, 1.1 moles of pyridine, and 500 ml of anhydrous ether. The mixture was refluxed for 2 hours. After cooling, to the mixture was added 200 ml of water, and the resulting mixture was extracted with ether. The ether layer was evaporated, and the resulting residue was distilled under reduced pressure to afford 1-alkoxycarbonyltricyclo [4.3.1.1$^{2,5}$]undecane.

The physical constants and varied spectral data of the thus obtained esters of a variety of alcohols are shown in Table 2.

Table 2

| Products [R in the formula(I)] | Boiling point (°C.) | Elemental Analysis | Calculated Found | IR (cm$^{-1}$) | MS (relative intensity) |
|---|---|---|---|---|---|
| CH$_3$ | 115/2 mmHg | C: 74.96 C: 75.20 | H: 9.68 H: 9.51 | 3030, 2900, 1723, 1480, 1255, 1215, 1205, 1075 | 208(M$^+$, 22), 149(81), 141(72), 93(29), 91(18), 83(19), 79(33), 67(100) |
| n-C$_4$H$_9$ | 142/3 mmHg | C: 76.75, C: 76.82, | H: 10.47 H: 10.32 | 3025, 2900 1723, 1465, 1255, 1208 1075 | 250(M$^+$, 22), 183(26), 149(17), 127(38), 93(23), 83(28), 81(47) 79(25), 67(100) |
| n-C$_8$H$_{17}$ | 167/2 mmHg | C: 78.38, C: 78.42, | H: 11.18 H: 11.22 | 3030, 2950, 1723, 1464, 1250, 1208, 1075 | 306(M$^+$, 20), 239(14), 195(36), 194(21), 149(91), 127(40), 81(42), 79(21), 67(100) |
|  | 135/1 mmHg | C: 77.82, C: 77.93, | H: 9.99 H: 10.10 | 3030, 2950, 1722, 1470, 1280, 1255, 1210, 1090, 1070, 1040 | 262(M$^+$, 3), 195(37), 194(55), 149(100), 127(29), 93(19), 83(18), 81(38), 79(21), 67(97) |
| 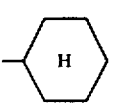 | 158/1 mmHg | C: 78.21, C: 78.32, | H: 10.21 H: 10.10 | 3025, 2925, 2850, 1720, 1460, 1440, 1310, 1280, 1250, 1220, 1210, 1180, 1150, 1070, 980 | 276(M$^+$, 6), 195(70) 194(61), 149(78), 127(28), 93(18), 83(37), 81(41), 67(100), 55(39) |

Table 2-continued

| Products [R in the formula(I)] | Boiling point (°C.) | Elemental Analysis | Calculated Found | IR (cm$^{-1}$) | MS (relative intensity) |
|---|---|---|---|---|---|
| ![structure] | 162/0.5 mmHg | C: 80.44, C: 80.58, | H: 9.83 H: 9.72 | 3030, 2930, 2850, 1720, 1475, 1440, 1250, 1230, 1210, 1070, 980 | 328(M$^+$, 3), 195(20), 149(100), 135(69), 134(816), 93(16), 81(25), 79(19), 67(86), 66(21) |

What is claimed as new and intended to be covered by letters patent is:

1. Tricyclo[4.3.1.1$^{2,5}$]undecane-1-carboxylic acid and acid halides and esters thereof represented by the formula (I),

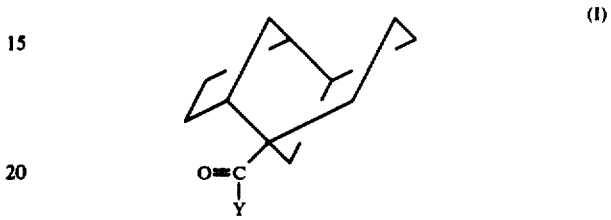

wherein Y represents a hydroxy group, a chlorine or bromine atom, or an alkoxyl group of the formula RO— wherein R is a straight-chain, branched-chain or cyclic alkyl group having 1 to 12 carbon atoms.

2. 1-Alkoxycarbonyltricyclo[4.3.1.1$^{2,5}$]undecane according to claim 1, wherein R represents a straight-chain alkyl group having 1 to 8 carbon atoms, or a cyclopentyl, cyclohexyl or exo-5,6-trimethyleneorborn-2-yl group.

* * * * *